United States Patent [19]

Tanaka et al.

[11] Patent Number: 4,586,901
[45] Date of Patent: May 6, 1986

[54] METHOD AND INSTRUMENT FOR CONDENSING RESTORATIVE DENTAL MATERIALS

[75] Inventors: John S. Tanaka, Menlo Park; William M. Belef, Mountain View, both of Calif.

[73] Assignee: Shofu Dental Corporation, Menlo Park, Calif.

[21] Appl. No.: 659,243

[22] Filed: Oct. 10, 1984

[51] Int. Cl.⁴ .................................................. A61C 3/08
[52] U.S. Cl. ........................................ 433/164; 433/147
[58] Field of Search ........................ 433/164, 166, 147

[56] References Cited

U.S. PATENT DOCUMENTS

| | | | |
|---|---|---|---|
| 159,173 | 1/1875 | Gaillard | 433/164 |
| 532,720 | 1/1895 | Dennis | 433/164 |
| 532,721 | 1/1895 | Dennis | 433/164 |
| 691,763 | 1/1902 | Harper | 433/164 |
| 1,579,968 | 4/1926 | Taylor | 433/164 |
| 1,676,715 | 7/1928 | Snyder | 433/164 |
| 2,603,871 | 7/1952 | Call | 433/164 |
| 4,306,864 | 12/1981 | Law | 433/164 |

FOREIGN PATENT DOCUMENTS 26988  9/1902  Switzerland ........................ 433/164

Primary Examiner—John J. Wilson
Attorney, Agent, or Firm—Thomas Schneck

[57] ABSTRACT

A dental condensing instrument having an elastomeric tip of sufficient size to surround the margins of a prepared cavity, which will yieldably urge the flow of soft restorative materials inside prepared cavities to improve their adaptation to cavity walls and margins without the introduction of deleterious air voids therein. When hand pressure is applied, the tip will not only seal said margins, but also apply a steady, isostatic condensing force upon said materials.

4 Claims, 13 Drawing Figures

METHOD AND INSTRUMENT FOR CONDENSING RESTORATIVE DENTAL MATERIALS

DESCRIPTION

1. Technical Field

The invention relates to dentistry and more particularly to a hand-held dental condensing instrument having a disposable elastomeric condensing tip.

2. Background Art

Hand instruments for condensing dental materials are well known. Such instruments typically have an elongated handle and at least one cylindrical condensing head emanating from the end of the handle and bent relative thereto. The head is made of metal or of any unyielding plastic, to condense dental materials such as silver amalgam alloys. Condensation is accomplished by repetitively striking such materials with said head in order to compress their volumetric size inside prepared cavities.

For condensing soft, plastic dental restorative material, such as polymer composite, use of such an unyielding instrument head is not ideal because repetitive striking action introduces tiny air pockets into said restorative, thus compromising its integrity. Furthermore, unlike silver amalgam, a composite cannot resist the striking action of the condenser head; the action will merely cause displacement of the composite without condensing it.

An object of the present invention is to provide a method of, and an instrument for, condensing dental restorative materials inside a prepared cavity under substantially isostatic pressure, to not only prevent the introduction of deleterious air voids on the surfaces of said materials, but also to improve their adaptation to cavity walls and margins.

SUMMARY OF THE INVENTION

When condensing a soft restorative material, it is more desirable to use an elastomeric condenser tip which is yieldable to hand pressure. The diameter of the tip should be sufficiently oversized so that it could not only surround the cavity preparation, but also support the condensing force of the central portion of the tip. As will be seen momentarily, it is desirable that the tip surface facing said material be in a concave relationship thereto. Under sufficient hand pressure, it can be readily seen that the outer area of the tip will initially deform and adapt itself to the infinitely variable anatomy of the tooth structure surrounding said cavity and substantially seal the perimeter of the cavity. Under constant, increasing hand pressure, the central portion of the tip will move into said cavity filled with a mass of said material. Since the perimeter of said cavity is sealed by said outer portion of the tip, the material is subjected to an isostatic force which compels it to adapt more tightly to cavity walls and margins without the introduction of deleterious air voids. Such a condensing method will produce a restoration of superior density and integrity. The tips are disposable and may be selectable in size and anatomy to suit different situations in the dental operatory.

BEST MODE FOR CARRYING OUT THE INVENTION

Figure 1:
FIG. 1 is a side view of the condensing instrument of the present invention. It is shown approximately normal size.

With reference to FIG. 1, the dental instrument 11 features an elongated handle 12 similar in dimensions to amalgam condensing instruments of prior art. The handle has cylindrical portions 13 and 14, terminal portions 15 and 16 which are bent at an angle away from the main handle body, and mandrel ends 17 and 18 supporting the elastomeric tips 19 and 20. The diameter of the tapered ends of the instrument is usually a few millimeters or less. The elastomeric tips 19 and 20 attach to the end mandrels 17 and 18 by friction or other means, such as by an interlocking relationship. These tips are easily disposable after use.

Figure 2:
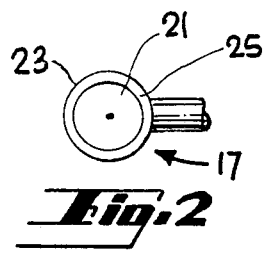
FIGS. 2 and 3 are frontal plan views of the ends of the instrument shown in FIG. 1.
Figure 3:
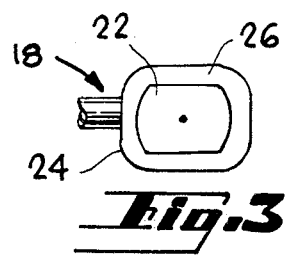

FIGS. 2 and 3 show the end mandrels 17 and 18. End buttons 21 and 22 support the elastomeric tips and the collars 23 and 24 form shoulders 25 and 26 that provide additional support for the elastomeric tips. The end buttons are reduced diameter regions relative to the mandrel ends.

Figure 4:
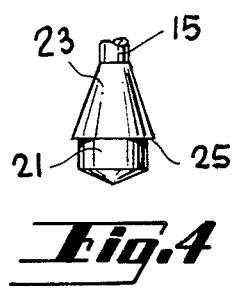
FIGS. 4–7 are side plan views of the instrument ends or mandrels and alternate ends or mandrels.
Figure 7:
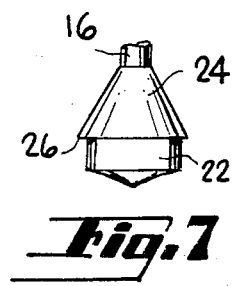

FIGS. 4 and 7 show terminal portions 15 and 16 attached to collars 23 and 24, respectively, which in turn, are attached to button-shaped mandrels 21 and 22. The ends are generally cylindrical, of outside diameter less than the diameter of the collar. Each collar is generally conical in shape with the cone apex joined to the tapered terminal portions of the instrument and the cone base joined to the end buttons. In FIG. 7, the end is of larger size than in FIG. 4 for supporting a larger elastomeric tip.

Figure 5:
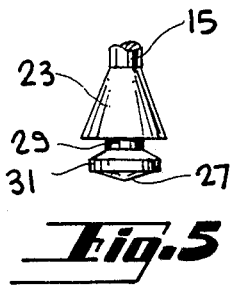
Figure 6:
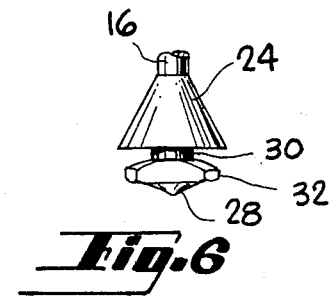

The details of FIGS. 5 and 6 show an optional end design. As in FIGS. 4 and 7, the terminal portions 15 and 16 are attached to the conical collars 23 and 24. The end buttons 27 and 28 are joined to the base of the conical collars at a diameter less than that of the buttons themselves. This creates circumferential undercuts 29 and 30 that allow the elastomeric tips to be wrapped over rims 31 and 32 in an interlocking relationship.

Figure 8:
FIGS. 8–11 are side plan views of the elastomeric tips for attaching to the mandrels (instrument ends) illustrated in FIGS. 4–7 respectively.
Figure 9:
Figure 10:
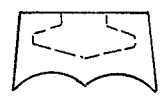
Figure 11:
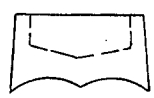
Figure 12:
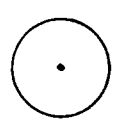
FIGS. 12 and 13 are frontal plan views of the elastomeric tips illustrated in FIGS. 8 and 11 respectively.
Figure 13:
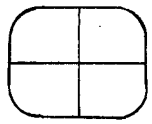

FIGS. 8–11 show various size elastomeric tips which fit over the button-shaped mandrels and receive support from the bases of the conical collars. Each elastomeric tip has opposed sides, one side having an opening, indicated by dashed lines, which seats a corresponding button-shaped mandrel and holds it in place by a friction or overlocking fit onto the mandrel. The opposite side is a tooth-contacting convex surface which is generally pointed. A portion of this surface is intended to fit into the depression on the top surface of the tooth and exert downward pressure on the composite restorative material placed in the tooth. The elastomeric nature of the tip allows a spreading of the material. A preferred tip material is silicon rubber of a moderaly soft texture, although the texture is a matter of choice, as is the shape of the tip. FIGS. 8 and 9 show tips having a generally conical shape, as indicated by the frontal view of FIG. 12. On the other hand, the tips of FIGS. 10 and 11 have four quadrants, each sloping from a central apex point as shown in FIG. 13. A shape may be selected to impress a desired tooth anatomy on the restoration material.

The instrument of the present invention is used in a dental operatory after a cavity has been prepared and soft dental restorative material placed into the prepared cavity. An elastomeric tip in accord with the present invention which is sufficiently oversize is connected to a handle and seated above the prepared cavity having an unformed mass of the restorative material. When hand pressure is applied, the tip will deform and seal the perimeter of the cavity preparation, or as a minimum, the margins or borders of the cavity. The margins are the outermost cut regions of a cavity, while the perimeter of a cavity preparation is the border just beyond the margins. Then, as further pressure is applied the tip will be forced into the restorative material to urge the material under isostatic pressure to move outwardly to adapt itself to cavity walls and margins.

We claim:

1. A dental instrument to condense a soft restorative material inside a cavity preparation having walls and peripheral margins comprising, an elongated handle having at least one end bent at an angle thereto, and an elastomeric tip removably attached to said end, the tip being sufficiently oversize with raised peripheral regions to surround and seal the entire perimeter of a cavity preparation, and having a raised central region to urge said material to adapt to the cavity walls and margins under hand pressure, the peripheral regions of the tip being resiliently deformable to deform to continue to surround and seal the cavity preparation when said central region is moved to urge said material.

2. The instrument of claim 1 wherein the surface of the tip contacting said preparation is preformed to impress a desired tooth anatomy on said material.

3. The instrument of claim 1 wherein the surface of said tip facing said material is in a concave relationship thereto.

4. The method of condensing a soft dental restorative material inside a prepared cavity, having walls, peripheral margins and a perimeter just beyond said margins, comprising the steps of:

(1) providing an elastomeric tip having a raised central portion to condense restorative material and a raised peripheral outer portion sufficiently oversize to rest upon a tooth structure and completely surround said cavity, the cavity having an unformed mass of restorative material therein, (2) applying sufficient, constant hand pressure to cause the outer portion of said tip to deform and substantially seal said perimeter, then (3) applying further hand pressure to force the tip into and isostatically urging said material to adapt to cavity walls and margins.

* * * * *